United States Patent
Zhang et al.

(10) Patent No.: US 8,814,358 B1
(45) Date of Patent: Aug. 26, 2014

(54) BINOCULAR ADAPTIVE OPTICS VISUAL SIMULATOR AND METHOD FOR BINOCULAR ADAPTIVE OPTICS VISUAL SIMULATION

(71) Applicant: Institute of Optics and Electronics, Chinese Academy of Sciences, Sichuan (CN)

(72) Inventors: Yudong Zhang, Sichuan (CN); Jian Kang, Sichuan (CN); Yun Dai, Sichuan (CN); Haoxin Zhao, Sichuan (CN); Bo Liang, Sichuan (CN); Fei Xiao, Sichuan (CN); Junlei Zhao, Sichuan (CN)

(73) Assignee: Institute of Optics and Electronics, Chinese Academy of Sciences, Sichuan (CN)

( * ) Notice: Subject to any disclaimer, the term of this patent is extended or adjusted under 35 U.S.C. 154(b) by 0 days.

(21) Appl. No.: 14/079,852

(22) Filed: Nov. 14, 2013

(30) Foreign Application Priority Data

Aug. 2, 2013 (CN) .......................... 2013 1 0333017

(51) Int. Cl.
*A61B 3/10* (2006.01)
*A61B 3/00* (2006.01)

(52) U.S. Cl.
CPC .................................. *A61B 3/0025* (2013.01)
USPC ............................ 351/221; 351/204; 351/246

(58) Field of Classification Search
CPC .. G02B 2027/0132; A61B 3/10; A61B 3/113; A61B 3/112; G01B 2290/50
USPC .................................. 315/221, 204, 246, 205
See application file for complete search history.

(56) References Cited

U.S. PATENT DOCUMENTS

| | | | |
|---|---|---|---|
| 5,543,866 A * | 8/1996 | Van de Velde | 351/221 |
| 5,784,145 A * | 7/1998 | Ghodse et al. | 351/205 |
| 7,559,652 B2 | 7/2009 | Lindacher | |
| 2007/0139614 A1 | 6/2007 | Lindacher | |
| 2011/0242483 A1 | 10/2011 | Shea et al. | |

FOREIGN PATENT DOCUMENTS

WO 2007/071401 A1 6/2007
WO 2012/154278 A1 11/2012

OTHER PUBLICATIONS

Arines, Pupil tracking with a Hartmann-Shack wavefront sensor, Journal of Biomedical Optics 15(3), 036022 (May/Jun. 2010), p. 1-7.
Sahin et al., Adaptive optics with pupil tracking for high resolution retinal imaging, Biomedical Optics Express vol. 3, No. 2, Feb. 1, 2012, p. 225-239.

(Continued)

*Primary Examiner* — Hung Dang
(74) *Attorney, Agent, or Firm* — Posz Law Group, PLC

(57) ABSTRACT

A binocular adaptive optics visual simulator and a method for binocular adaptive optics visual simulation are provided. An example method may comprise: directing beacon light to a left eye and a right eye of a subject, respectively; sensing aberrations of the left and right eyes of the subject, and sensing a deflection angle of a pupil of each of the left and right eyes; correcting the aberrations based on the sensed aberrations to achieve a desired aberration configuration between the left and right eyes; and changing a direction in which the beacon light is directed based on the sensed deflection angle in such a manner that in a case where the pupil is subjected to deflection, the beacon light is incident onto the pupil of each of the left and right eyes of the subject at a substantially identical angle before and after the deflection of the pupil.

15 Claims, 5 Drawing Sheets

(56) References Cited

OTHER PUBLICATIONS

Liang et al., Supernormal vision and high-resolution retinal imaging through adaptive optics. J. Opt. Soc. Am. A, 1997. 14(11): p. 2884-2892 (discussed on p. 1 of the specification).

Fernández et al., Study on the effects of monochromatic aberrations in the accommodation response by using adaptive optics. J. Opt. Soc. Am. A, 2005. 22(9): p. 1732-1738 (discussed on p. 1 of the specification).

Lixia et al., Higher-Order Aberrations Correction and Vision Analysis System for Human Eye. Acta Optica Sinica, 2007. 27(5): p. 893-897 (with English abstract) (discussed on p. 1-2 of the specification).

Fernández et al., Binocular adaptive optics visual simulator. Optics Letters, 2009. 34(17): p. 2628-2630 (discussed on p. 2 of the specification).

Chen et al., Accommodation with higher-order monochromatic aberrations corrected with adaptive optics, J. Opt. Soc. Am. 2006.V23(1), p. 1-8 (discussed on p. 2 of the specification).

Gambra et al., Accommodative lag and fluctuations when optical aberrations are manipulated, Journal of Vision 2009.9(6), p. 1-15 (discussed on p. 2 of the specification).

\* cited by examiner

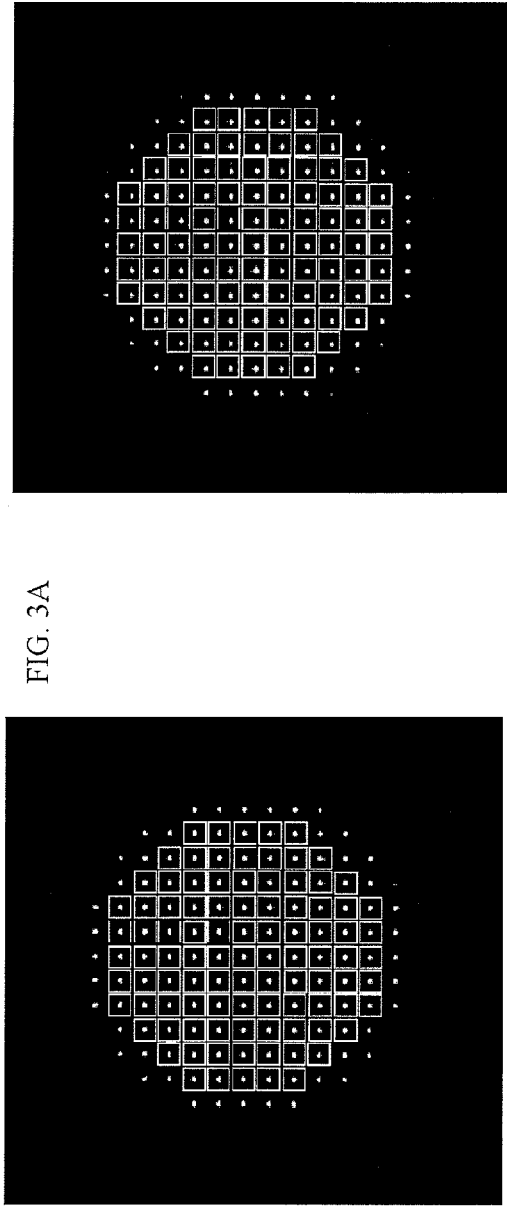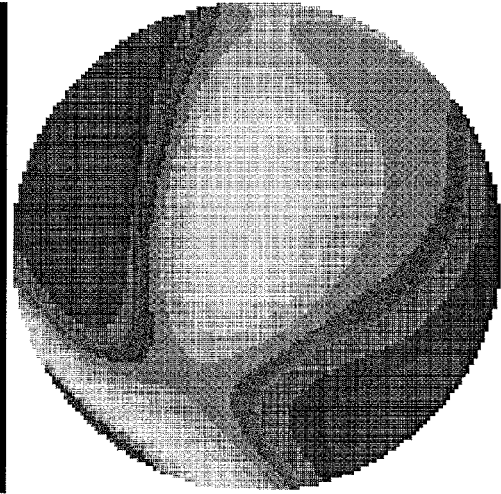
FIG. 3A
FIG. 3B

BINOCULAR ADAPTIVE OPTICS VISUAL SIMULATOR AND METHOD FOR BINOCULAR ADAPTIVE OPTICS VISUAL SIMULATION

TECHNICAL FIELD

The present disclosure generally relates to the field of adaptive optics, and more particularly, to a binocular adaptive optics visual simulator and a method for binocular adaptive optics visual simulation, by which it is possible to track eye movements.

BACKGROUND

Wavefront aberrations of human eyes have been focused on by visual researches for a long time. In 1997, Liang and Williams firstly incorporated a Hartmann sensor into an adaptive optics system to achieve static compensation for the aberrations of the human eyes and thus to achieve supernormal vision (Liang, J., D. R. Williams, and D. T. Miller, Supernormal vision and high-resolution retinal imaging through adaptive optics. J. Opt. Soc. Am. A, 1997. 14(11): p. 2884-2892). As the adaptive optics technology proves to be successful in the visual optics field, there are more and more researches in the role of high-order aberrations of the human eyes in visual functions.

An Adaptive Optics Visual Simulators (AOVS) is an important tool in the visual optics researches. The AOVS simulates effects of the aberrations of the human eyes in the visual functions by measuring variations of the visual functions of the human eyes under different states of aberrations. In 2001, research groups from Rochester University, United States and from Murcia University, Spain independently proposed schemes for closed-loop dynamic correction of the aberrations. Thereafter, many researchers employ AOVS's to explore relationships between the aberrations of the human eyes and the visual functions (Fernández, E. J. and P. Artal, Study on the effects of monochromatic aberrations in the accommodation response by using adaptive optics. J. Opt. Soc. Am., A, 2005. 22(9): p. 1732-1738; Lixia, X., et al., Higher-Order Aberrations Correction and Vision Analysis System for Human Eye. ACTA OPTICA SINICA, 2007. 27(5): p. 893-897). Those visual simulators are all monocular systems. However, binocular vision is a normal case for the human eyes. Therefore, it is natural and necessary for the researches to transit from monocular vision to binocular vision. For example, in 2009, E. J. Fernández, et al. from Murcia University, Spain proposed a binocular adaptive optics visual simulator for researches on contrast sensitivities when there are different combinations of spherical aberrations superimposed on a pair of eyes (Fernández, E. J., P. M. Prieto, and P. Artal, Binocular adaptive optics visual simulator. OPTICS LETTERS, 2009. 34(17): p. 2628-2630). Later, Ramkumar Sabesan, et al. from Rochester University, United States proposed in 2010 a binocular adaptive optics visual simulator for researches on effects of binocular aberrations on visual acuities and contrast sensitivities.

Recent researches show that accommodative lag of the eyes is directly relevant to myopia (L. Chen, P. B. Kruger, H. Hofer, B. Singer, and D. R. Williams, Accommodation with higher-order monochromatic aberrations corrected with adaptive optics, J. Opt. Soc. Am. 2006.V23(1), 1-8). Further, some of the high-order aberrations of the human eyes are closely associated with causes of the accommodative lag (E. Gambra, L. Sawides, C. Dorronsoro, and S. Marcos, Accommodative lag and fluctuations when optical aberrations are manipulated, Journal of Vision 2009.9(6), 1-15). Therefore, researches on effects of the aberrations of the human eyes on accommodation responses are valuable for exploring of causes and also clinic prevention and treatment of myopia. However, in a natural visual field, accommodation, vergence and pupil constriction are associated with each other, and precise cooperation among them is necessary for a single clear binocular vision. Here, "vergence" refers to that the two eyes focus on an external object by adjusting an angle included between their respective lines of sight, to achieve a single binocular vision. The above binocular visual simulators proposed by Murcia University and Rochester University are both based on a far viewing state where visual axes of the two eyes are parallel to each other, and thus are unsuitable for researches on the accommodation responses.

SUMMARY

In view of the above, an object of the present disclosure is to provide a binocular adaptive optics visual simulator and a method for binocular adaptive optics visual simulation, by which it is possible to track eye movements.

According to an aspect of the present disclosure, there is provided a binocular adaptive optics visual simulator, comprising a left-eye light-path simulator and a right-eye light-path simulator configured identically to each other. Each of the left-eye light-path simulator and the right-eye light-path simulator may comprise: a beacon light generator configured to emit beacon light; a scan mirror configured to direct the beacon light from the beacon light generator to a left eye or a right eye of a subject; a wavefront corrector configured to receive light resulting from reflection of the beacon light by an eyeground of the left or right eye of the subject and traveling in a first light path; a wavefront sensor configured to receive and sense the light from the wavefront corrector traveling in a second light path; a control unit configured to generate a drive signal for the wavefront corrector and a drive signal for the scan mirror based on a sensing result; a driver for the wavefront corrector configured to drive the wavefront corrector based on the drive signal for the wavefront corrector; and a driver for the scan mirror configured to drive the scan mirror based on the drive signal for the scan mirror in such a manner that in a case where a pupil of the subject is subjected to deflection, the beacon light is incident onto the pupil of the left or right eye of the subject at a substantially identical angle before and after the deflection of the pupil.

The binocular adaptive optics visual simulator may further comprise a visual target display device configured to generate a visual target, which is incident onto the left and right eyes of the subject in a third light path and a fourth light path, respectively. The third light path may pass through the wavefront corrector of the left-eye light-path simulator, and the fourth light path may pass through the wavefront corrector of the right-eye light-path simulator.

The beacon light generator may comprise a beacon light source configured to emit light, and a collimator lens configured to convert the light generated by the beacon light source into parallel light beams.

The binocular adaptive optics visual simulator may further comprise a first beam splitter configured to direct the parallel light beams converted by the collimator lens to the scan mirror. The first light path may comprise a light path starting from the eyeground, then passing though the scan mirror, the first beam splitter, a beam expanding lens group, a first reflector, and then arriving at the wavefront corrector. The second light path may comprise a light path starting from the wavefront corrector, then passing through a second reflector, a beam compressing lens group, a second beam splitter, a third reflector, and then arriving at the wavefront sensor.

Each of the third and fourth light paths may comprise a light path starting from the visual target display device, then passing through an imaging optical system, a rectangular prism, a fourth reflector, the second beam splitter, the beam compressing lens group, the second mirror, the wavefront corrector, the first reflector, the beam expanding lens group, the first beam splitter and the scan mirror, and then arriving at the left or right eye of the subject.

The visual target display device may be configured to generate visual targets at different spatial frequencies, different contrasts and/or different parallax.

The driver for the scan mirror may be configured to rotate and translate the scan mirror. For example, the driver for the scan mirror may be configured to translate the scan mirror in a straight line perpendicular to and/or parallel to an optical axis of the beacon light incident thereon.

The binocular adaptive optics visual simulator may further comprise a defocusing plate disposed between each of the left and right eyes of the subject and the corresponding scan mirror and configured to eliminate effects of chromatic aberrations caused by a wavelength difference between the beacon light and light carrying the visual target.

The binocular adaptive optics visual simulator may further comprise a straight sliding guide. The visual target display device may be configured to slide along the straight sliding guide to generate visual targets of different defocus.

The wavefront sensor may be selected from a Hartmann wavefront sensor based on a micro-prism array, a Hartmann wavefront sensor based on a micro-lens array, a pyramid sensor, and a curvature sensor.

The wavefront corrector may be selected from a deformable mirror, a liquid crystal wavefront modulator, a micromachined membrane deformable mirror, micro electromechanical deformable mirror, a bimorph deformable mirror, a liquid deformable mirror.

According to a further aspect of the present disclosure, there is provided a method for binocular adaptive optics visual simulation, comprising: directing beacon light to a left eye and a right eye of a subject, respectively; sensing aberrations of the left and right eyes of the subject, and sensing a deflection angle of a pupil of each of the left and right eyes; correcting the aberrations based on the sensed aberrations to achieve a desired aberration configuration between the left and right eyes; and changing a direction in which the beacon light is directed based on the sensed deflection angle in such a manner that in a case where the pupil is subjected to deflection, the beacon light is incident onto the pupil of each of the left and right eyes of the subject at a substantially identical angle before and after the deflection of the pupil.

The directing of the beacon light may be achieved by a scan mirror, and changing the direction in which the beacon light is directed may comprise rotating and translating the scan mirror.

The method may further comprise directing light resulting from reflection of the beacon light by an eyeground of each of the left and right eyes to a wavefront sensor via a wavefront corrector, wherein sensing of the aberrations and the deflection angle is achieved by the wavefront sensor, and correcting of the aberrations is achieved by the wavefront corrector.

According to embodiments of the present disclosure, it is possible to extract information on the deflection angle of the pupil of each of the left and right eyes from spot distribution in an aberrometric image of the wavefront sensor. Based on the extracted information on the deflection angle, it is possible to drive both the scan mirrors to be rotated and translated accordingly, so that the beacon light, after being reflected by the scan mirrors, is incident onto the pupils at the same angle, resulting in real-time tracking of the left and right eyes. Thus, it is possible not only to perform precise binocular visual function tests in a near viewing state where eye axes of the two eyes cross each other, but also to effectively eliminate errors caused by involuntary deflections of the eye axes of the subject in a far viewing state where the eye axes of the two eyes are parallel to each other, so as to improve accuracy and precision of the binocular visual function tests.

BRIEF DESCRIPTION OF THE DRAWINGS

The above and other objects, features and advantages of the present disclosure will become more apparent from the following descriptions of embodiments thereof, with reference to attached drawings, in which:

FIG. 3a is a schematic view showing spots on a wavefront sensor in a state where eyeballs are not rotated according to an example;

FIG. 3b is a schematic view showing spots on a wavefront sensor in a state where eyeballs are rotated according to an example;

In the drawings, to distinguish left and right eyes, suffixes of "L" and "R" are used to indicate respective components for the left and right eyes. Throughout the drawings, like reference symbols may indicate like components.

DETAILED DESCRIPTION

Hereinafter, embodiments of the present disclosure will be described with reference to the attached drawings. It is to be understood, however, that the following descriptions are provided only for illustrative purposes, instead of limiting the present disclosure. Further, in the following descriptions, configurations and techniques which are well known to those skilled in the art may be omitted to avoid unnecessarily obscuring the concept of the present disclosure.

Figure 1:
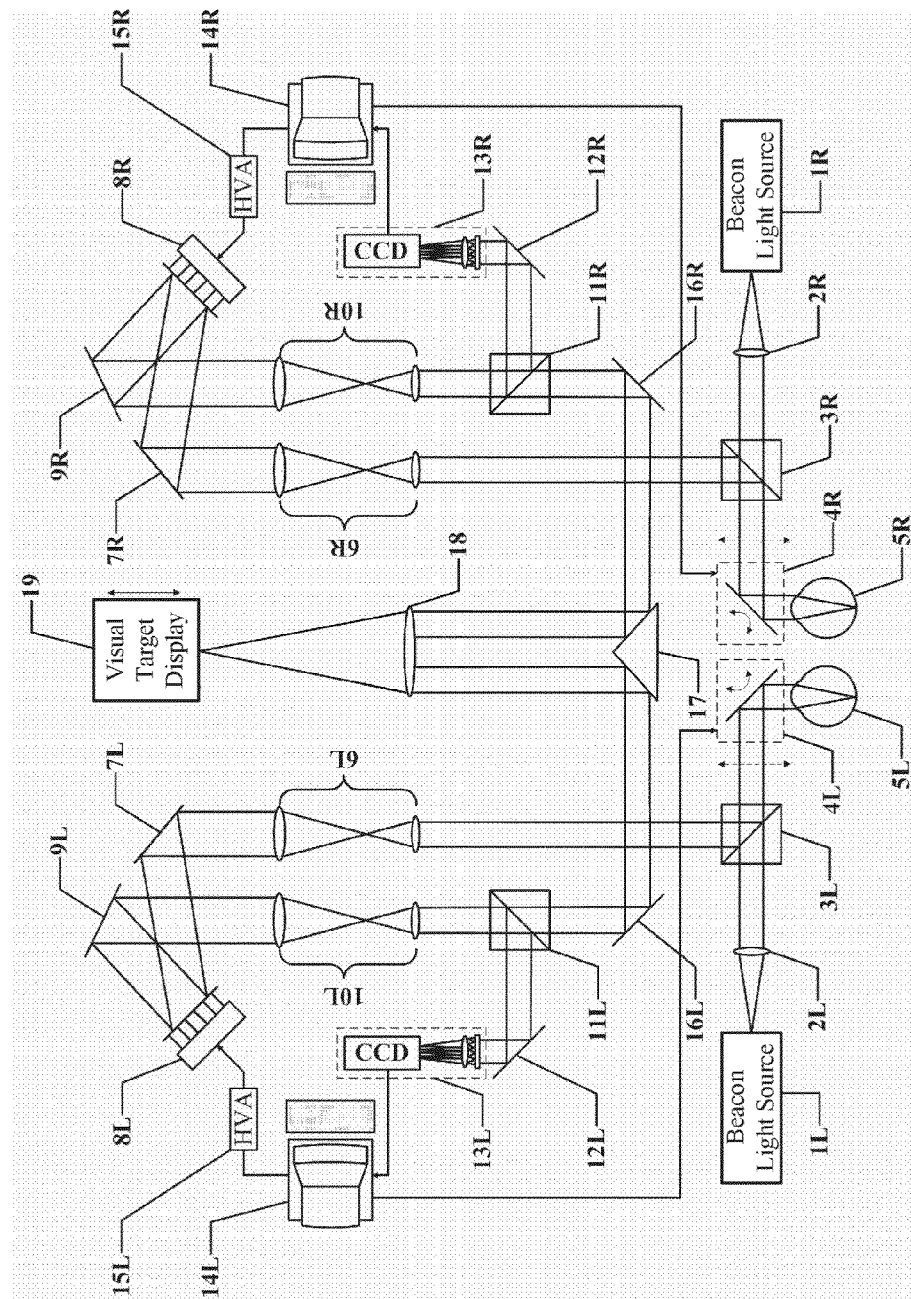
FIG. 1 is a schematic view showing a configuration of a binocular adaptive optics visual simulator according to an embodiment of the present disclosure.

FIG. 1 is a schematic view showing a configuration of a binocular adaptive optics visual simulator according to an embodiment of the present disclosure.

As show in FIG. 1, the binocular adaptive optics visual simulator according to this embodiment may comprise two simulators for left and right eyes of a subject, respectively. That is, there may be a left-eye light-path simulator and a right-eye light-path simulator, which can be identically configured. For example, each of the simulators may comprise a beacon light generator, a scan mirror, a wavefront corrector, a wavefront sensor, a control unit, a driver for the wavefront corrector, and a driver for the scan mirror.

The beacon light generator may be configured to generate beacon light. For example, the beacon light generator may comprise a beacon light source 1L/1R. In an example, the beacon light source 1L/1R may comprise a near infrared laser at a wavelength of about 905 nm. In this way, it is possible to avoid interferences on the eyes of the subject in visual function measurements.

For better measurements, the beacon light generator may further comprise a collimator lens 2L/2R. The collimator lens 2L/2R can be configured to convert the light emitted from the beacon light source 1L/1R into parallel light beams. In a case where the beacon light source 1L/1R is able to emit parallel light beams (for example, a surface light source which is capable of emitting parallel beams), the collimator lens 2L/2R can be even omitted.

In the example in FIG. 1, two beacon light sources 1L and 1R are shown for the left-eye light-path and the right-eye light-path. However, the present disclosure is not limited thereto. For example, it is possible to provide only one beacon light source. Light emitted from this light source may be split by a splitter into two paths of beacon light for the left and right eyes, respectively.

The scan mirrors 4L/4R may be configured to direct the beacon light from the beacon light generator to the left eye 5L or the right eye 5R of the subject. The scan mirror 4L/4R may comprise a reflector. According to an embodiment, the scan mirror 4L/4R may be supported by a moving mechanism, and thus is movable, for example, rotatable and/or translatable.

In an example, to better fit with a subsequent light path as will be described in the following, there may be a first beam splitter 3L/3R provided between the beacon light generator (in this example, the collimator lens 2L/2R) and the scan mirror 4L/4R. For example, the beacon light may transmit through the first beam splitter 3L/3R and then be incident onto the scan mirror 4L/4R.

The wavefront corrector 8L/8R may be configured to receive light resulting from reflection of the beacon light by an eyeground of the left eye or the right eye of the subject. To direct the reflected light to the wavefront corrector, there may be various light directing components such as reflectors. Further, to match sizes among various components, there may be also various beam transforming components, such as beam expanding/compressing lens groups. In the example of FIG. 1, the light reflected from the eyeground (and thus carrying information about aberrations of the left eye or right eye of the subject) may be reflected by the scan mirror 4L/4R onto the first beam splitter 3L/3R, then further be reflected by the first beam splitter 3L/3R, pass through a beam expanding lens group 6L/6R, and further be reflected by a first reflector 7L/7R onto the wavefront corrector 8L/8R. Hereinafter, the light path from the eyeground to the wavefront corrector 8L/8R is referred to as "a first light path."

Although FIG. 1 shows a specific example of the first light path, the present disclosure is not limited thereto. It is apparent for those skilled in the art that there are various means for directing light from one component to another component. For example, it is possible to deflect the light path by providing a reflector, a prism, or the like, and/or to alter beam characteristics (for example, parallel beam or converging or diverging beam, beam diameter, and the like) by providing a lens or the like. This is also true for the following descriptions of light paths and their constituting components. These descriptions are provided to make the present disclosure comprehensive and complete, but not for limiting the present disclosure.

The wavefront corrector 8L/8R may be configured to correct a wavefront of the light, so as to correct the aberrations of the left or right eye or to achieve any desired aberration configuration between the two eyes, which will be described in further detail in the following. For example, the wavefront corrector 8L/8R may be selected from a deformable mirror, a liquid crystal wavefront modulator, a micromachined membrane deformable mirror, micro electromechanical deformable mirror, a bimorph deformable mirror, a liquid deformable mirror.

The wavefront sensor 13L/13R may be configured to receive the light from the wavefront corrector 8L/8R. For example, the light reflected by the eyeground may be incident on the wavefront corrector 8L/8R and then further reflected by the wavefront corrector 8L/8R, and the reflected light can be received by the wavefront sensor 13L/13R. As described above, to direct the light from the wavefront corrector 8L/8R to the wavefront sensor 13L/13R, there may be various light directing components, such as reflectors. Further, to match sizes among various components, there may be various beam transforming components, such as beam expanding/compressing lens groups. In the example in FIG. 1, the light reflected from the wavefront corrector 8L/8R (and carrying the information about the aberrations of the left eye or right eye of the subject) may be reflected by a second reflector 9L/9R, pass through a beam compressing lens group 10L/10R, further be reflected by a second beam splitter 11L/11R, and then further be reflected by a third reflector 12L/12R onto the wavefront sensor 13L/13R. Hereinafter, the light path from the wavefront corrector 8L/8R to the wavefront sensor 13L/13R is referred to as "a second light path."

Although FIG. 1 shows a specific example of the second light path, the present disclosure is not limited thereto, as described above.

The wavefront sensor 13L/13R may be configured to sense the received light. For example, the wavefront sensor 13L/13R may sense the information on the aberrations of the left or right eye of the subject carried by the received light. In an example, the wavefront sensor 13L/13R may be selected from a Hartmann wavefront sensor based on a micro-prism array, a Hartmann wavefront sensor based on a micro-lens array, a pyramid sensor, and a curvature sensor.

According to an advantageous example of the present disclosure, the wavefront sensor 13L/13R may be further configured to sense a deflection angle of a pupil of the left or right eye of the subject. For example, it is possible to determine information about eyeball rotation based on light spots on the wavefront sensor. Before the eyeball rotation, the light spots are located at substantially a center of each of sub-apertures of the wavefront sensor. In this case, a horizontal tilt A1 and a vertical tilt A2 are both approximately 0, as shown in FIG. 3a. After the eyeball rotation, the light spots on the wavefront sensor are displaced so as not to be located at the center of each of the sub-apertures. Thus, the horizontal tilt A1 and the vertical tilt A2 are no longer 0, as shown in FIG. 3b. The deflection angle of the pupil can be determined based on these displacements.

The control unit 14L/14R may be configured to control whole operations of the simulator. For example, the control unit 14L/14R may be configured to receive a sensing result from the wavefront sensor 13L/13R, and generate various control commands based on the sensing result. In an example, the control unit 14L/14R may be configured to generate a drive signal for the wavefront corrector based on the aberrations of the left or right eye sensed by the wavefront sensor 13L/13R, and to generate a drive signal for the scan mirror based on the deflection angle sensed by the wavefront sensor 13L/13R.

The control unit 14L/14R may comprise various computing devices, such as processors or microprocessors, controllers or microcontrollers, application specific integrated circuits, or the like. In the example of FIG. 1, the control unit 14L/14R is illustrated as a personal computer (PC) with an input device such as keyboard. However, the present disclosure is not limited thereto.

The driver 15L/15R for the wavefront corrector may be configured to receive a control signal from the control unit 14L/14R, and drive the wavefront corrector 8L/8R accordingly. For example, the driver 15L/15R for the wavefront corrector may be configured to drive the wavefront corrector 8L/8R based on the drive signal for the wavefront corrector, so as to correct the aberrations of the left or right eye or to achieve any desired aberration configurations between the two eyes. In the example in FIG. 1, the driver 15L/15R for the wavefront corrector is illustrated as a high voltage amplifier (HVA). However, the present disclosure is not limited thereto. Any suitable driver 15L/15R for the wavefront corrector can be used based on a type of the wavefront corrector 8L/8R being used.

The driver for the scan mirror (which is illustrated in FIG. 1 together with the scan mirror as a movable scan mirror 4L/4R) may be configured to receive a control signal from the control unit 14L/14R, and drive the scan mirror 4L/4R accordingly. For example, the driver for the scan mirror may be configured to drive the scan mirror based on the drive signal for the scan mirror in such a manner that the beacon light is incident onto the pupil of the left or right eye of the subject at a substantially identical angle before and after the pupil is deflected. The driver for the scan mirror can be implemented as any suitable moving mechanism, such as, a rotating and/or translating mechanism or the like. In this way, it is possible to achieve real-time tracking of the left and right eyes.

According to an advantageous example, the above simulator may further have a visual target display device 19 incorporated therein, to test visual functions of the two eyes of the subject. The visual target display device 19 may be configured to generate a visual target to stimulate the left and right eyes of the subject. The visual target may be generated at different special frequencies, different contrasts, and/or different parallax. For example, the visual target may comprise a static or dynamic image. The visual target display device 19 may comprise a display such as a projector display. Alternatively, the visual target display device 19 may be implemented even as a picture such as an eye chart.

The visual target generated by the visual target display device 19 may be shown to the subject, especially, via the above described optical system. For example, in the example in FIG. 1, the visual target may be shown to the subject through an imaging optical system 18, a rectangular prism 17, a fourth reflector 16L/16R, the second beam splitter 11L/11R, the beam compressing lens group 10L/10R, the second reflector 9L/9R, the wavefront corrector 8L/8R, the first reflector 7L/7R, the beam expanding lens group 6L/6R, the first beam splitter 3L/3R and the scan mirror 4L/4R. Hereinafter, the light paths from the visual target display device 19 to the left eye and the right eye of the subject are referred to as "a third light path" and "a fourth light path," respectively.

As described above, although FIG. 1 shows specific examples of the third and fourth light paths and the third/fourth light path travels in a direction substantially opposite to the first and second light paths, the present disclosure is not limited thereto. The visual target generated by the visual target display device 19 can be presented to the left and right eyes of the subject through any suitable light paths, provided that they pass through the wavefront corrector 8L/8R. Preferably, the third light path and the fourth light path have a substantially identical optical length, and have a substantially identical optical magnification. Generally, the third light path and the fourth light path can be symmetrical to each other.

In an example, a defocusing plate may be disposed between the eye 5L/5R of the subject and the scan mirror 4L/4R, for eliminating effects of chromatic aberrations caused by a wavelength difference between the beacon light and light carrying the visual target. Further, to be suitable for binocular visual tests relating to accommodation responses, the visual target display device 19 may be slid along a straight sliding guide, to generate visual targets of different defocus, so as to induce accommodation responses of the human eyes.

Figure 2:
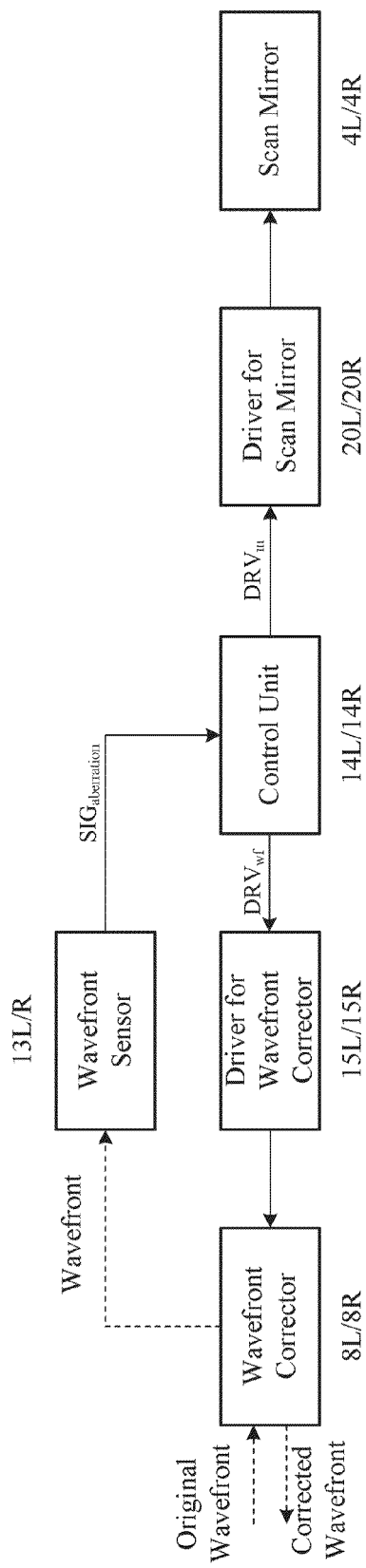
FIG. 2 is a block diagram schematically showing a control system for a binocular adaptive optics visual simulator according to an embodiment of the present disclosure.

FIG. 2 illustrates a control system for operations of the binocular adaptive optics visual simulator of FIG. 1. In FIG. 2, dashed arrows are used to show optical signals, and solid arrows are used to show electrical signals. Referring to FIGS. 1 and 2, in operation, the beacon light source 1L/1R emits light, which passes through the collimator lens 2L/2R, the first beam splitter 3L/3R, and the scan mirror 4L/4R, and then enters into the eye 5L/5R of the subject. The light is reflected by the eyeground and thus carries the information about the aberrations of the left or right eye. The reflected light passes through the scan mirror 4L/4R, the first beam mirror 3L/3R, the beam expanding lens group 6L/6R, and the first reflector 7L/7R, and then impinges onto the wavefront corrector 8L/8R. From the wavefront corrector 8L/8R, the light further travels forward through the second reflector 9L/9R, the beam compressing lens group 10L/10R, the second beam splitter 11L/11R, and the third reflector 12L/12R to be incident onto the wavefront sensor 13L/13R. The wavefront sensor 13L/13R senses the received light to generate a sense signal $S_{aberration}$ (indicating, for example, the aberrations of the left or right eye and also the deflection angle of the pupil of the subject), and delivers the sense signal $S_{aberration}$ to the control unit 14L/14R. The control unit 14L/14R may generate a drive signal $DIV_{wf}$ for the wavefront corrector based on the sense signal $S_{aberration}$, and send the drive signal $DIV_{wf}$ to the driver 15L/15R (for example, HVA) for the wavefront corrector. The driver 15L/15R for the wavefront corrector may drive the wavefront corrector 8L/8R based on the drive signal $DIV_{wf}$, to correct the aberrations of the left or right eye or to achieve any desired aberration configuration between the two eyes. On the other hand, the control unit 14L/14R may generate a drive signal $DIV_m$ for the scan mirror based on the sense signal $S_{aberration}$, and send the drive signal $DIV_m$ to the driver 20L/20R for the scan mirror. The driver 20L/20R for the scan mirror may drive the scan mirror 4L/4R based on the drive signal $DIV_{wf}$ to be rotated and translated accordingly, so that the beacon light reflected by the scan mirror is incident on the pupil at the substantially same angle, in order to achieve real-time tracking of the left and right eyes.

Figure 4:
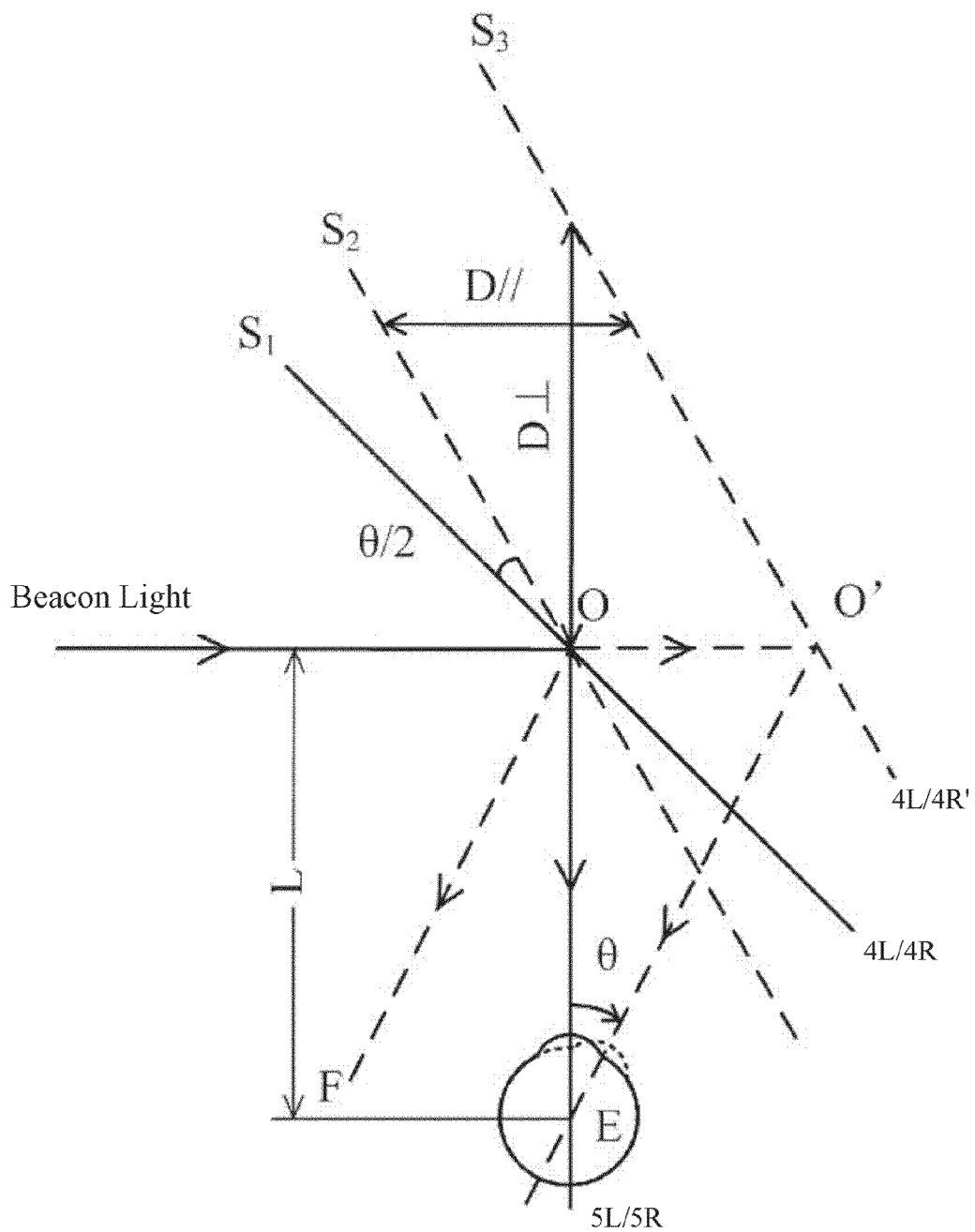
FIG. 4 is a schematic view showing movements of a scan mirror for tracking purpose.

FIG. 4 is a schematic view showing movements of the scan mirror for tracking purpose. Initially, the scan mirror 4L/4R is located at S1, and the beacon light is incident on the scan mirror at a certain angle, for example, 45°, and then enters the left or right eye 5L/5R along an eye axis OE. If the eye axis is rotated by an angle of θ from OE to O'E, the beacon light will not be incident on the eye along the eye axis. To achieve tracking of eye movements, it is desired to adjust the scan mirror in terms of rotation angle and location so that the beacon light, after being reflected by the scan mirror, can enter the eye 5L/5R of the subject along the new eye axis O'E. Generally, in mirror reflecting, if an incident direction is not changed while a reflecting surface is rotated by an angle of φ, then reflected light will be rotated by an angle of 2φ in the same direction. Therefore, if the scan mirror is rotated by an angle of φ/2 in the same direction to S2, and a reflected version OF of the beacon light from the scan mirror will be parallel to the current eye axis O'E. Thus, if the scan mirror is translated to S3, the reflected version of the beacon light from the scan mirror 4L/4R' will enter the eye 5L/5R of the subject along the new eye axis O'E. It is to be noted that the scan mirror can be translated in a direction parallel to the incident direction of the beacon light, or a direction perpendicular to the incident direction of the beacon light, or any other suitable straight or even curved line. Let a maximal rotation angle of the eyeball be $\phi_{max}$, a distance between a rotation center of the eyeball and a center of the scan mirror be L, and a diameter of the light beam be a. Here, L may be considered as a sum of a radius (about 12 mm) an anteroposterior axis of the eyeball and a distance from the pupil to the center of the scan mirror. If the scan mirror is translated in the direction parallel to the incident direction of the beacon light, then a maximal movement distance is:

$$D_\| = L \tan \theta_{max}.$$

In this case, the scan mirror has a diameter that needs to satisfy:

$$A_\| > a/\sin(\theta_{max}/2 + 45°).$$

If the scan mirror is translated in the direction perpendicular to the incident direction of the beacon light, then a maximal movement distance is:

$$D_\perp = D_\| \tan(\theta_{max}/2 + 45°).$$

In this case, the scan mirror has a diameter that needs to satisfy:

$$A_\perp > (a + D_\perp)/\sin(\theta_{max}/2 + 45°).$$

In an example, the maximal rotation angle of the eyeball is $\theta_{max} = 20°$, the distance between the rotation center of the eyeball and the center of the scan mirror is L=42 mm, and the diameter of the light beam is a=6 mm. In this case, $$\begin{cases} D_\| = 7.28 \text{ mm}, \\ A_\| > 7.32 \text{ mm}, \\ D_\perp = 10.40 \text{ mm}, \\ A_\perp > 20 \text{ mm}, \end{cases}$$

Therefore, it is preferable to translate the scan mirror in the direction parallel to the incident direction of the beacon light, resulting in a relatively shorter movement distance. Further, in this case the light beam can be incident onto the center of scan mirror, and thus it is possible to adopt the scan mirror with a relatively smaller diameter, resulting in a reduced cost.

Figure 5:
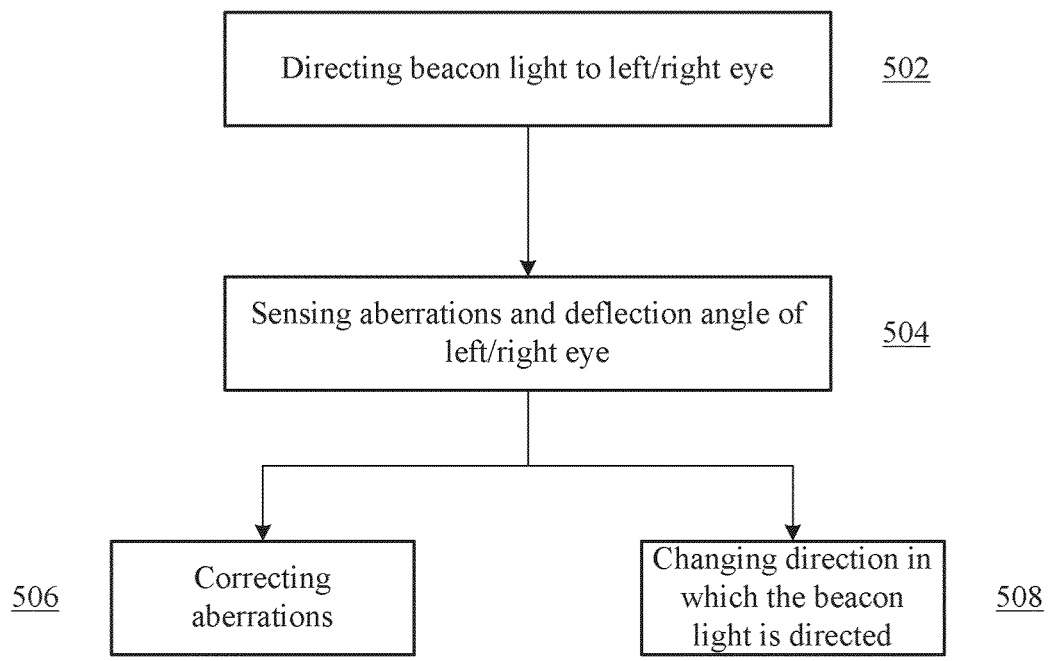
FIG. 5 is a flow chart showing a method for binocular adaptive optics visual simulation according to an embodiment of the present disclosure.

According to a further embodiment of the present disclosure, there is further provided a method for binocular adaptive optics visual simulation. As shown in FIG. 5, the method may comprise at 502 directing beacon light into a left eye and a right eye of a subject, respectively. The beacon light may be generated by a beacon light source (such as the beacon light source 1L/1R as described above), and can be directed to the eyes through a series of optic components (such as the collimator lens 2L/2R, the first beam splitter 3L/3R, and the scan mirror 4L/4R, as described above). The beacon light can be reflected by an eyeground of each of the eyes, and thus the reflected light may carry information on aberrations of the left and right eyes and also information on pupil deflection.

The method may further comprise at 504 sensing the aberrations of the left and right eyes and also a pupil deflection angle from the reflected light. Such sensing can be performed by means of, for example, a wavefront sensor (such as the wavefront sensor 13L/13R as described above). The reflected light can be directed to the wavefront sensor in a certain light path (such as the first light path+the second light path as described above). The light path can pass through a wavefront corrector (such as the wavefront corrector 8L/8R as described above).

The method may further comprise at 506 correcting the aberrations based on the sensed aberrations. Such correction may be performed by means of, for example, a wavefront corrector (such as the wavefront corrector 8L/8R as described above). In an example where the light arrives at the wavefront sensor via the wavefront corrector, it is possible for the wavefront sensor to further sense the corrected aberrations.

Further, the method may comprise at 508 changing a direction in which the beacon light is directed based on the sensed deflection angle so that the beacon light is incident onto the pupil of the left or right eye at the substantially same angle before and after the pupil is deflected. For example, such changing may be performed by rotation and translation of a scan mirror.

It is to be noted that the method is not limited to be achieved by the arrangement shown in FIG. 1, but is applicable to any suitable binocular adaptive optics visual simulator.

According to embodiments of the present disclosure, the eye movements can be tracked in the binocular visual simulation. Thus, it is possible to track rotations of the eyeballs in a real-time manner in binocular visual tests. As a result, it is possible to perform effective binocular visual function tests in a near viewing state where eye axes of the two eyes cross each other, and also to effectively eliminate affects of errors caused by involuntary deflections of the eye axes of the subject in a far viewing state where the eye axes of the two eyes are parallel to each other, so as to improve accuracy and precision of the binocular visual function tests.

From the foregoing, it will be appreciated that specific embodiments of the disclosure have been described herein for purposes of illustration, but that various modifications, substitutions and additions may be made without deviating from the disclosure. Therefore, the technology is not limited except as by the appended claims.

We claim:

1. A binocular adaptive optics visual simulator, comprising a left-eye light-path simulator and a right-eye light-path simulator configured identically to each other, wherein each of the left-eye light-path simulator and the right-eye light-path simulator comprises:
   a beacon light generator configured to emit beacon light;
   a scan mirror configured to direct the beacon light from the beacon light generator to a left eye or a right eye of a subject;
   a wavefront corrector configured to receive light resulting from reflection of the beacon light by an eyeground of the left or right eye of the subject and traveling in a first light path;
   a wavefront sensor configured to receive and sense the light from the wavefront corrector traveling in a second light path;
   a control unit configured to generate a drive signal for the wavefront corrector and a drive signal for the scan mirror based on a sensing result;
   a driver for the wavefront corrector configured to drive the wavefront corrector based on the drive signal for the wavefront corrector; and
   a driver for the scan mirror configured to drive the scan mirror based on the drive signal for the scan mirror in such a manner that in a case where a pupil of the subject is subjected to deflection, the beacon light is incident onto the pupil of the left or right eye of the subject at a substantially identical angle before and after the deflection of the pupil.

2. The binocular adaptive optics visual simulator according to claim 1, further comprising a visual target display device configured to generate a visual target, which is incident onto the left and right eyes of the subject in a third light path and a fourth light path, respectively, wherein the third light path passes through the wavefront corrector of the left-eye light-path simulator, and the fourth light path passes through the wavefront corrector of the right-eye light-path simulator.

3. The binocular adaptive optics visual simulator according to claim 2, wherein the beacon light generator comprises:
a beacon light source configured to emit light; and
a collimator lens configured to convert the light generated by the beacon light source into parallel light beams.

4. The binocular adaptive optics visual simulator according to claim 3, further comprising a first beam splitter configured to direct the parallel light beams converted by the collimator lens to the scan mirror;
wherein the first light path comprises a light path starting from the eyeground, then passing though the scan mirror, the first beam splitter, a beam expanding lens group, a first reflector, and then arriving at the wavefront corrector; and
wherein the second light path comprises a light path starting from the wavefront corrector, then passing through a second reflector, a beam compressing lens group, a second beam splitter, a third reflector, and then arriving at the wavefront sensor.

5. The binocular adaptive optics visual simulator according to claim 4, wherein each of the third and fourth light paths comprises a light path starting from the visual target display device, then passing through an imaging optical system, a rectangular prism, a fourth reflector, the second beam splitter, the beam compressing lens group, the second mirror, the wavefront corrector, the first reflector, the beam expanding lens group, the first beam splitter and the scan mirror, and then arriving at the left or right eye of the subject.

6. The binocular adaptive optics visual simulator according to claim 2, wherein the visual target display device is configured to generate visual targets at different spatial frequencies, different contrasts and/or different parallax.

7. The binocular adaptive optics visual simulator according to claim 2, further comprising a defocusing plate disposed between each of the left and right eyes of the subject and the corresponding scan mirror and configured to eliminate effects of chromatic aberrations caused by a wavelength difference between the beacon light and light carrying the visual target.

8. The binocular adaptive optics visual simulator according to claim 2, further comprising a straight sliding guide, wherein the visual target display device is configured to slide along the straight sliding guide to generate visual targets of different defocus.

9. The binocular adaptive optics visual simulator according to claim 8, wherein the wavefront corrector is selected from a deformable mirror, a liquid crystal wavefront modulator, a micromachined membrane deformable mirror, micro electromechanical deformable mirror, a bimorph deformable mirror, a liquid deformable mirror.

10. The binocular adaptive optics visual simulator according to claim 1, wherein the driver for the scan mirror is configured to rotate and translate the scan mirror.

11. The binocular adaptive optics visual simulator according to claim 10, wherein the driver for the scan mirror is configured to translate the scan mirror in a straight line perpendicular to and/or parallel to an optical axis of the beacon light incident thereon.

12. The binocular adaptive optics visual simulator according to claim 1, wherein the wavefront sensor is selected from a Hartmann wavefront sensor based on a micro-prism array, a Hartmann wavefront sensor based on a micro-lens array, a pyramid sensor, and a curvature sensor.

13. A method for binocular adaptive optics visual simulation, comprising:
directing beacon light to a left eye and a right eye of a subject, respectively;
sensing aberrations of the left and right eyes of the subject, and sensing a deflection angle of a pupil of each of the left and right eyes;
correcting the aberrations based on the sensed aberrations to achieve a desired aberration configuration between the left and right eyes; and
changing a direction in which the beacon light is directed based on the sensed deflection angle in such a manner that in a case where the pupil is subjected to deflection, the beacon light is incident onto the pupil of each of the left and right eye of the subject at a substantially identical angle before and after the deflection of the pupil.

14. The method according to claim 13, wherein the directing of the beacon light is achieved by a scan mirror, and changing the direction in which the beacon light is directed comprises rotating and translating the scan mirror.

15. The method according to claim 13, further comprising directing light resulting from reflection of the beacon light by an eyeground of each of the left and right eyes to a wavefront sensor via a wavefront corrector, wherein sensing of the aberrations and the deflection angle is achieved by the wavefront sensor, and correcting of the aberrations is achieved by the wavefront corrector.

* * * * *